US00PP09836P

United States Patent [19]

Wuhl

[11] Patent Number: Plant 9,836

[45] Date of Patent: Mar. 25, 1997

[54] "MATINEE" PLUM TREE

[76] Inventor: Eric Wuhl, 5480 E. Lane, Fresno, Calif. 93727

[21] Appl. No.: 582,287

[22] Filed: Jan. 3, 1996

[51] Int. Cl.[6] ..... A01H 5/00

[52] U.S. Cl. ..... Plt./38.1

[58] Field of Search ..... Plt./38.1

[56] References Cited

U.S. PATENT DOCUMENTS

P.P. 8,037 11/1992 Wuhl ..... Plt./38.1

*Primary Examiner*—James R. Feyrer

[57] ABSTRACT

A new distinct variety of plum tree which is somewhat remotely similar to the "Santa Rosa" plum tree (unpatented), but from which it is distinguished by producing uniformly larger fruit which are mature for harvesting and shipment approximately one week earlier than the "Santa Rosa" plum tree and exhibits superior holding ability as compared with that of the "Santa Rosa" plum tree and having yellower flesh with red coloration just under the skin.

1 Drawing Sheet

BACKGROUND OF THE NEW VARIETY

This present invention relates to a new and distinct variety of plum tree, *Prunus salicina* which will hereinafter be denominated varietally as the "Matinee" plum tree, and more particularly to a plum tree which produces fruit which are mature for commercial harvesting and shipment approximtely thirteen days before the "Santa Rosa" plum tree (unpatented), or about June 5 to about June 10 in the San Joaquin Valley of Central California, and which further is distinguished principally as to novelty by producing uniformly larger fruit which have yellower flesh than that of the "Santa Rosa" plum tree, a brighter red skin coloration, and which can hold on the tree and stay firm to a higher level of maturity.

The "Santa Rosa" plum tree has been one of the most commercially successful varieties of plum tree over many decades producing large fruit having pleasingly colored and flavorful flesh ripening for harvest approximately June 18 in the San Joaquin Valley of Central California. The "Santa Rosa" plum tree remains in many respects the standard by which other varieties are judged.

However, the "Santa Rosa" plum tree has some traits which are less than desirable. For example, the "Santa Rosa" plum tree is frequently characterized by premature fruit drop which makes harvesting a particularly critical operation and, of course, reduces the volume of the crop which can successfully be harvested.

The "Matinee" plum tree of the present invention possesses many of the same attractive characteristics of the "Santa Rosa" plum tree producing fruit red to purple coloration, and shape. However, the fruit of the instant variety is uniformly larger and has flesh of a consistently yellower coloration. It is further distinguished from the "Santa Rosa" plum tree in that the fruit of the "Matinee" plum tree consistently holds on the tree and remains firm considerably longer than that of the "Santa Rosa" plum tree.

ORIGIN AND ASEXUAL REPRODUCTION OF THE NEW VARIETY

The present variety of the plum was discovered by the inventor in 1992 as an open pollinated seedling of the "Showtime" plum tree (U.S. Plant Pat. No. 8,037) in the inventor's orchard located in Fresno, Calif. The new variety was selected from five hundred and eighteen (518) seedlings. The new variety was asexually reproduced at the inventor's direction in 1993 by budding onto "Nemaguard" rootstock in Fresno County in June of the year. The resulting asexually reproduced trees were planted in an orchard located on the inventor's property in Fowler, Calif. Those trees have been observed by the inventor since that time and have confirmed that the distinctive characteristics of the parent tree of the new variety are in all respects reproduced in its progeny.

SUMMARY OF THE VARIETY

The "Matinee" plum tree is characterized as to novelty by producing a medium-sized fruit generally of a red skin coloration for commercial harvesting and shipment June 5 to June 10 in the San Joaquin Valley of Central California. The new and novel variety is most closely similar to the "Showtime" plum tree (U.S. Plant Pat. No. 8,037) from which it was derived as a newly found seedling, but from which it is distinguished and characterized as to novelty by producing uniform fruit having redder skin, yellower flesh with red coloration just under the skin and having a superior holding ability avoiding the occasional premature fruit drop characteristic of the "Showtime" plum tree.

BRIEF DESCRIPTION OF THE DRAWINGS

The drawing is a color photograph showing mature fruit of the new variety of the present invention, including first shown top view thereof the apex; then a second, shown in the side view (elevation); a third shown sectioned along the suture plane with the stone in place; a fourth shown sectioned along the suture with the stone in place; and fifth shown exposing the suture of the plum fruit. A representative leaf is shown in a top-plane view; a second leaf shown in bottom view; a representative twig, the stone, and a section of the bark—all of the new variety.

DETAILED DESCRIPTION

Referring more specifically to the pomological details of this new and distinct variety of plum tree, the following details have been observed under the ecological conditions prevailing at the orchard of origin, which is located near Fresno in the San Joaquin Valley of Central California. All major color code designations are by reference to the

*Dictionary of Color* by Maerz and Paul, First Edition, 1930. Common color names are also occasionally employed.

TREE

Generally:
- *Size.—Medium.*
- *Vigor.*—Not overly vigorous.
- *Chilling requirements.*—Approximately 800 hours below 45 degrees Fahrenheit. Similar to other plum varieties.
- *Figure.*—Upright.
- *Producivity.*—Productive.
- *Regularity of bearing.*—Regular
- *Internode length.*—Approximately 30 mm (1.181 inches).

Trunk:
- Size.—Stocky.
- *Growth habit.*—Upright. Angle of scaffold branches to the central leader is seventeen degrees (17°) to eighty-five degrees (85°).
- *Density.*—Open and sprawling. Develops whips.
- *Surface texture.*—Medium.
- *Color.*—Page 39, Plate 8, A-10, Sepia.
- *Lenticels—numbers.*—Numerous.
- *Lenticels—size.*—Small, 0.5 mm (0.019 inches).

Branches:
- Size.—Medium.
- *Surface texture—Mature.*—Medium, similar to trunk.
- *Surface texture—Immature.*—Smooth.
- *Color—one year or older wood.*—Page 33, Plate 5, D-9, Roseglow.
- *Color—immature branches.*—Page 49, Plage 13, D-7, Oakbluff.
- *Lenticels—generally.*—Variable depending upon age of branch.
- *Lenticels—numbers.*—Young shoots — very few.
- *Lenticels—numbers.*—Mature of older wood — several.
- *Lenticles—size.*—0.5 mm (0.019 inches) to 1 mm (0.039 inches) by 2 mm (0.078 inches) to 5 mm (0.196 inches).

LEAVES

Size: Medium.
Length: 111 mm±1.6 mm (4.37 inches±0.063 inches).
Width: 53 mm±1.4 mm (2.07 inches±0.055 inches).
Shape: Ovate.
Color:
- *Upwardly disposed surface.*—Page 67, Plate 22, H-8, Civette Gr.
- *Downwardly disposed surface.*—Page 63, Plate 20, C-6, Seaspray T.

Marginal form: Double serrate.
Glandular characteristics: Not always present. None on immature leaves. One or two on mature leaves. Small size.
Leaf vein:
- *Color.*—Page 49, Plate 13, A-5, Mavis Grain Brown.

*Thickness.*—1 mm.
Petiole:
- *Size.—Small to medium.*
- *Length.*—11 mm to 13 mm (0.43 inches to 0.52 inches).
- *Thickness.*—1 mm to 2 mm (0.039 inches to 0.078 inches).
- *Color.*—Green.

*Stem glands:*
- *Shape.*—Globose.
- *Position.*—Opposite and alternate.
- *Number.*—Two to five.
- *Color.*—Green.

Stipules: None

FLOWERS

Flower buds:
- *Size.*—Small, tender, conic in shape and short. Description is based on current season growth.
- *Surface texture.*—Glabrous.

Date of bloom: Popcorn stage, February 6, first bloom, February 9; fifty percent bloom, February 13; full bloom, February 20; petal fall, February 25.
Flower size: Small, 15 mm (0.59 inches) to 18 mm (0.71 inches) when open.
Showiness: Very showy.
Petals:
- *Color.*—White.

Pistil: One.
Stamen:
- *Number.*—23.

Pollen:
- *Color.*—Golden.
- *Quantity.*—Medium.

Self-fertility: Semi-self fruitful.

FRUIT

Maturity when described: Ripe for commercial harvest and shipment the first week of June in the San Joaquin Valley of Central California.
Size:
- *Generally.*—Medium size, uniform in size, shape and weight when lightly thinned and separate fruit in clusters.
- *Average diameter in the axial plane.*—56 mm (2.2 inches).
- *Average diameter in the suture plane.*—55 mm (2.165 inches).
- *Average diameter transverse and at right angles to the suture plane.*—55 mm (2.165 inches).
- *Form.*—Uniformity — Very uniform. Most of them are cordate (heart shaped).
- *Suture.*—Generally a very shallow, inconspicuous line extends from the base to the apex and is slightly deeper at cavity.
- *Ventral surface.*—Generally — Smooth, rounded.
- *Stem cavity*—generally.—Acute.
- *Stem cavity*—width.—14 )0.55 inches).
- *Stem cavity*—depth.—8 mm (0.315 inches).
- *Stem cavity*—length.—20 mm (0.79 inches).
- *Stem cavity*—shape.—Oval.
- *Stem.—generally* 8 mm to 10 mm long (0.315 inches to 0.39 inches).
- *Stem—caliper.*—1½ mm to 2 mm (0.056 inches to 0.078 inches).
- *Apex.*—Slightly rounded.
- *Pistol point.*—Position — Variable.

Skin:
- *Thickness.*—Thin.
- *Texture.*—Smooth.
- *Tendency to crack.*—None.
- *Color.*—Page 33, Plate 5, C-6, Afgan R Cheekerberry.

Flesh:
- *Flesh color.*—Yellow fleshed, with red coloration just under the skin.

*Flesh color—Near Apex.*—Page 135, Plate 56, L-12.
*Flesh color—Top of fruit immediately under shin.*—Page 133, Plate 55, L-8, Rubiente.
*Flesh color—Remainder.*—Page 43, Plate 10, K-5.
*Color of pit well.*—Page 33, Plate 5, C-6, Afgan R.
*Surface of pit cavity.*—Smooth.
*Juice production.*—Moderate, but no free-flowing juice.
*Flavor.*—Excellent, sweet, good balance between sugar and acid, distinct flavor.
*Aroma.*—Mild.
*Texture.*—Meaty, firm.
*Ripening.*—Even ripening throughout the fruit.
*Eating quality.*—Excellent, no bitter aftertaste.

Stone:
*Attachment.*—Semi-cling.
*Fibers.*—None.
*Size—Length.*—25 mm (0.98 inches).
*Size—Width.*—17 mm (0.67 inches).
*Size—Thickness.*—10 mm (0.39 inches).
*Form.—Oval.*
*Apex shape.*—Pointed, acute.
*Color (dry).*—Page 33, Plate 5, 9A Longchamps.
*Base.*—Shape — Flat.
*Sides.*—Generally — Equal.
*Ridges.*—Only on ventral side.
*Tendency to Split.*—None.

Use: Fresh market.
Keeping quality: Good to excellent. Fruit remained firm after two weeks out of cool storage.
Resistance to disease: No known resistance or unusual susceptibility to known insects or diseases.
Shipping and handling qualities: Very good. The fruit holds well on the tree and will ship and store well after harvest.

Although the new variety of plum tree possesses the described characteristics noted above as a result of the growing conditions prevailing near Fresno in the central portion of the San Joaquin Valley of California, it is to be undertood that variations of the usual magnitude and characteristics incident to changes in growing conditions, irrigation, fertilization, pruning, pest control, climatic variation and the like are to be expected.

Having thus described and illustrated my new variety of plum tree, what I claim as new and desire to be secured by Plant Letters Patent is:

1. A new and distinct variety of plum tree substantially as illustrated and described, and which is somewhat remotely similar to the "Santa Rosa" plum tree (unpatented), but which it is distinguished by producing uniformly larger, more colorful fruit, having a very firm flesh with a sweet flavor, not being bitter near the pit, and which are mature for commercial harvesting approximately the first week of June in the San Joaquin Valley of Central California.

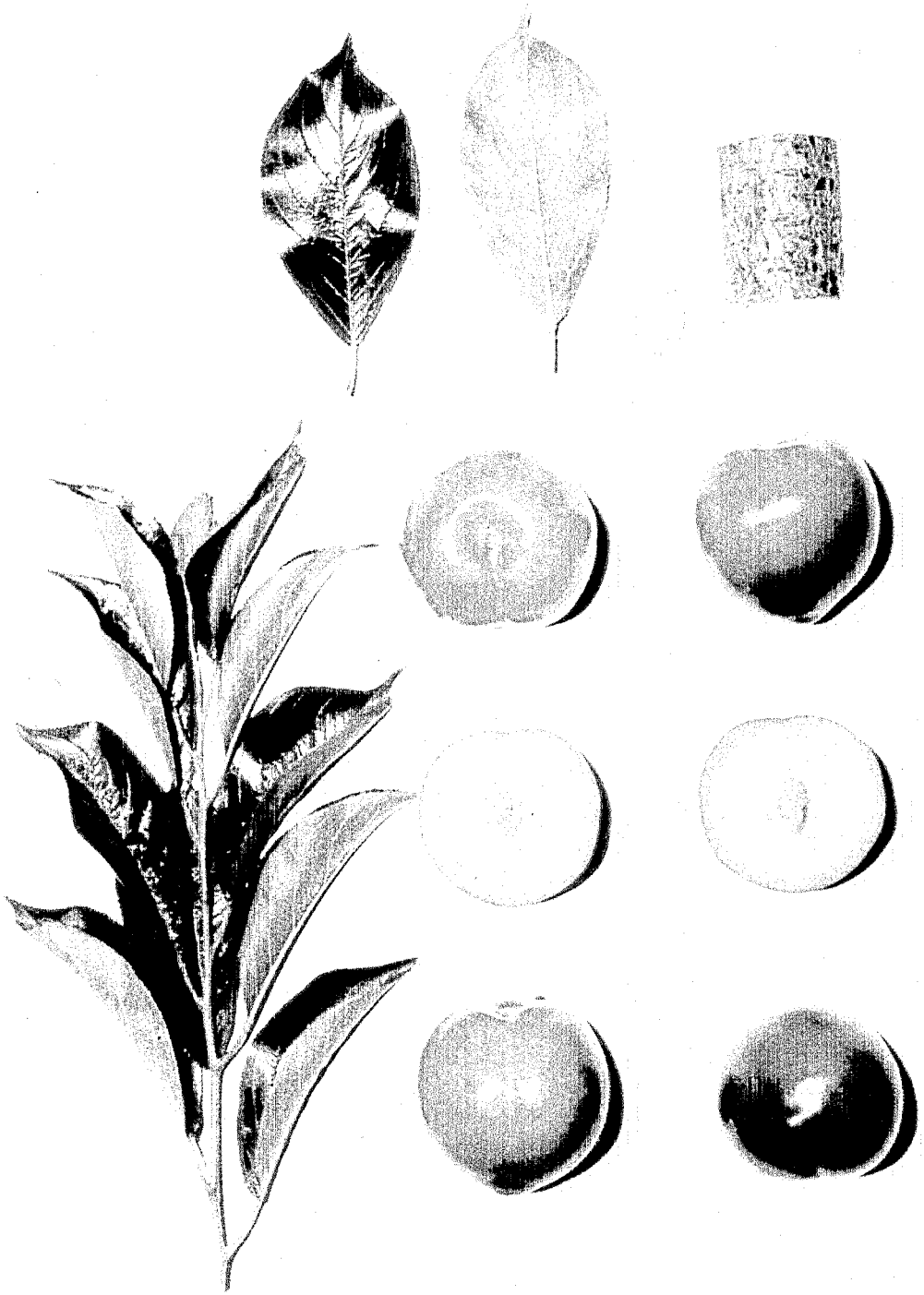

* * * * *